US009870871B1

(12) United States Patent
Campbell et al.

(10) Patent No.: US 9,870,871 B1
(45) Date of Patent: Jan. 16, 2018

(54) GRAPHENE MACRO-ASSEMBLY-FULLERENE COMPOSITE FOR ELECTRICAL ENERGY STORAGE

(71) Applicant: LAWRENCE LIVERMORE NATIONAL SECURITY, LLC, Livermore, CA (US)

(72) Inventors: Patrick G. Campbell, Oakland, CA (US); Theodore F. Baumann, Discovery Bay, CA (US); Juergen Biener, San Leandro, CA (US); Matthew Merrill, Dublin, CA (US); Elizabeth Montalvo, Oakland, CA (US); Marcus A. Worsley, Hayward, CA (US); Monika M. Biener, San Leandro, CA (US); Maira Raquel Cerón Hernández, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

(21) Appl. No.: 15/260,197

(22) Filed: Sep. 8, 2016

(51) Int. Cl.
*H01G 11/32* (2013.01)
*C07C 1/32* (2006.01)
(Continued)

(52) U.S. Cl.
CPC ......... *H01G 11/32* (2013.01); *C01B 31/0213* (2013.01); *C01B 31/0484* (2013.01);
(Continued)

(58) Field of Classification Search
CPC .... H01G 11/32; H01G 11/58; C01B 31/0213; C01B 31/0484; C07C 1/323; C07C 13/62;
(Continued)

(56) References Cited

U.S. PATENT DOCUMENTS 5,789,338 A 8/1998 Kaschmitter et al.
5,993,996 A 11/1999 Firsich
(Continued)

FOREIGN PATENT DOCUMENTS

WO WO-2013/132260 A2 9/2013

OTHER PUBLICATIONS

U.S. Appl. No. 14/820,411, filed Aug. 6, 2015, Lawrence Livermore National Security, LLC.
(Continued)

*Primary Examiner* — Daniel C McCracken
(74) *Attorney, Agent, or Firm* — Foley & Lardner LLP

(57) ABSTRACT

Disclosed here is a method for producing a graphene macro-assembly (GMA)-fullerene composite, comprising providing a GMA comprising a three-dimensional network of graphene sheets crosslinked by covalent carbon bonds, and incorporating at least 20 wt. % of at least one fullerene compound into the GMA based on the initial weight of the GMA to obtain a GMA-fullerene composite. Also described are a GMA-fullerene composite produced, an electrode comprising the GMA-fullerene composite, and a supercapacitor comprising the electrode and optionally an organic or ionic liquid electrolyte in contact with the electrode.

18 Claims, 6 Drawing Sheets

(51) Int. Cl.
*C07C 13/62* (2006.01)
*C01B 31/04* (2006.01)
*C01B 31/02* (2006.01)
*H01G 11/58* (2013.01)
*B82Y 40/00* (2011.01)
*B82Y 30/00* (2011.01)

(52) U.S. Cl.
CPC .............. *C07C 1/323* (2013.01); *C07C 13/62* (2013.01); *H01G 11/58* (2013.01); *B82Y 30/00* (2013.01); *B82Y 40/00* (2013.01); *C07C 2104/00* (2013.01); *Y10S 977/738* (2013.01); *Y10S 977/847* (2013.01); *Y10S 977/948* (2013.01)

(58) Field of Classification Search
CPC ..... C07C 2104/00; B82Y 30/00; B82Y 40/00; Y10S 977/738; Y10S 977/847; Y10S 977/948
USPC ......................................................... 423/448
See application file for complete search history.

(56) References Cited

U.S. PATENT DOCUMENTS

| | | |
|---|---|---|
| 6,491,789 B2 | 12/2002 | Niu |
| 6,522,522 B2 | 2/2003 | Yu et al. |
| 7,948,739 B2 | 5/2011 | Zhamu et al. |
| 2002/0182506 A1* | 12/2002 | Cagle .................... B82Y 30/00 429/231.8 |
| 2009/0061312 A1 | 3/2009 | Zhamu et al. |
| 2011/0124790 A1 | 5/2011 | Penicaud |
| 2012/0034442 A1 | 2/2012 | Pauzauskie et al. |
| 2012/0214000 A1 | 8/2012 | Kyrlidis et al. |
| 2013/0058008 A1 | 3/2013 | Kim et al. |
| 2014/0012034 A1 | 1/2014 | Shaffer et al. |
| 2014/0178289 A1 | 6/2014 | Worsley et al. |

OTHER PUBLICATIONS

Berger et al., "Ultrathin Epitaxial Graphite: 2D Electron Gas Properties and a Route toward Graphene-based Nanoelectronics," Journal of Physical Chemisty, vol. 108, No. 52, pp. 19912-19916.

Campbell et al., "Battery/supercapacitor hybrid via non-covalent functionalization of grapheme macro-assemblies," vol. 2, 2014, pp. 17764-17770.

Echegoyen et al., "Electrochemistry of Fullerenes and Their Derivatives," Accounts of Chemical Research, vol. 31, No. 9, 1998, pp. 593-601.

Sarma et al., "Electronic transport in two-dimensional graphene", Reviews of Modern Physics, vol. 83, No. 2, 2011, pp. 407-470.

Wang et al., "Preparation method of hydroquinone-formaldehyde carbon aerogels," High Power Laser and Particle Beams, vol. 17, No. 11, 2005, pp. 1709-1711, with English abstract.

Worsley et al., "Mechanically Robust 3D Graphene Macroassembly with High Surface Area," Chemical Community, vol. 48, 2012, pp. 8428-8430.

Worsley et al., "Synthesis and Characterization of Highly Crystalline Graphene Aerogels", ACS Nano, vol. 8, 2014, pp. 11013-11022.

Worsley et al., "Toward Macroscale, Isotropic Carbons with Graphene-Sheet-Like Electrical and Mechanical Properties," Advanced Functional Materials, vol. 24, 2014, pp. 4259-4264.

Wood et al., "Red-Absorbing Cationic Acceptor Dyes for Photocathodes in Tandem Solar Cells," The Journal of Physical Chemistry C, vol. 118, 2014, pp. 16536-16546.

* cited by examiner

Curcumin-Pyrene-C$_{60}$

Curcumin-Ferrocene-C$_{60}$

Curcumin-C$_{60}$

1-(4-aminophenyl)ethanone

GRAPHENE MACRO-ASSEMBLY-FULLERENE COMPOSITE FOR ELECTRICAL ENERGY STORAGE

FEDERAL FUNDING STATEMENT

The United States Government has rights in the invention pursuant to Contract No. DE-AC52-07NA27344 between the U.S. Department of Energy and Lawrence Livermore National Security, LLC, for the operation of Lawrence Livermore National Laboratory.

BACKGROUND

Supercapacitors (also known as ultracapacitors or electrical double-layer capacitors) have the potential to replace Li ion batteries as the next-generation electrical energy storage technology in demanding applications due to their high power density and excellent cycling stability. Graphene-based supercapacitor electrodes are particularly promising because they feature high surface area, good electrical conductivity, and chemical inertness. Researchers at Lawrence Livermore National Laboratory have developed binder-free 3D mesoporous graphene macro-assemblies (GMAs) that have exceptionally high surface area (~1500 $m^2/g$) and excellent conductivity (~100 S/m) using abundant and low cost starting materials. These GMAs offer many advantages over traditional carbon-based supercapacitor electrodes such as deterministic control over pore morphology, increased conductivity, and the absence of conductive filler and binder materials. However, the interfacial capacitance of graphene-based electrodes is limited by the low density of states at the Fermi level to ~10 $mF/cm^2$ (corresponding to 0.01 electron per carbon atom for the stability window of aqueous electrolytes). To replace Li-ion batteries in energy-demanding applications, these materials need improvements to their energy storage performance.

Fullerenes (also known as Bucky-balls) can store 10 times the energy per carbon as graphene (6 electrons per $C_{60}$ molecule or 1 electron per 10 carbon atoms). Since the discovery of $C_{60}$, fullerenes have attracted pronounced attention due to their applications in medicinal chemistry (as MM contrast agents, in tumor diagnosis and radio-immunotherapy), material science and photovoltaic solar cells, among others. Functionalization or chemical modification of fullerenes has be used to increase their solubility, allow their characterization and explore their physical and chemical properties. Fullerenes possess highly reactive double bonds that allow the study of their reactivity using different types of reactions, such as oxidation reactions, transition metal complexation, hydrogenations, halogenations, radical additions, cycloadditions (1,3-dipolar, [2+2], [4+2], [3+2], [2+2+1]), addition of nucleophiles (Bingel additions), sylilations and electrosynthesis.

SUMMARY

One aspect the invention described herein relates to a method for producing a GMA-fullerene composite, comprising providing a GMA comprising a three-dimensional network of graphene sheets crosslinked by covalent carbon bonds, and incorporating at least 20 wt. % of at least one fullerene compound into the GMA based on the initial weight of the GMA to obtain the GMA-fullerene composite.

In some embodiments, the fullerene compound is covalently bound to the graphene sheets. In some embodiments, the incorporating step comprises reacting the GMA with least one diazonium functionlized fullerene.

In some embodiments, the diazonium functionlized fullerene is represented by $F^*-(R)_n$, wherein: $F^*$ comprises a fullerene having a surface comprising six-membered and five-membered rings, R comprises a diazonium group and a conjugated linker covalently connecting the diazonium group to the fullerene, and n is at least one.

In some embodiments, n is 1 or 2, $F^*$ is $C_{60}$ or $C_{70}$, and R is selected from the group consisting of

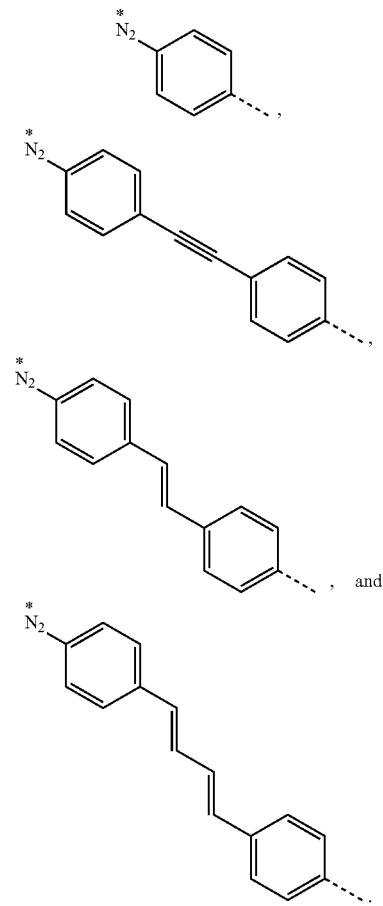

In some embodiments, the fullerene compound is noncovalently attached to the graphene sheets. In some embodiments, the incorporating step comprises incubating the GMA in a solution comprising at least one phenylamine functionlized fullerene.

In some embodiments, the phenylamine functionlized fullerene is represented by $F^*-(R)_n$, wherein: $F^*$ comprises a fullerene having a surface comprising six-membered and five-membered rings, R comprises a phenylamine group and a conjugated linker covalently connecting the phenylamine group to the fullerene, and n is at least one.

In some embodiments, n is 1 or 2, $F^*$ is $C_{60}$ or $C_{70}$, and R is selected from the group consisting of

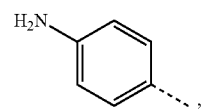

-continued

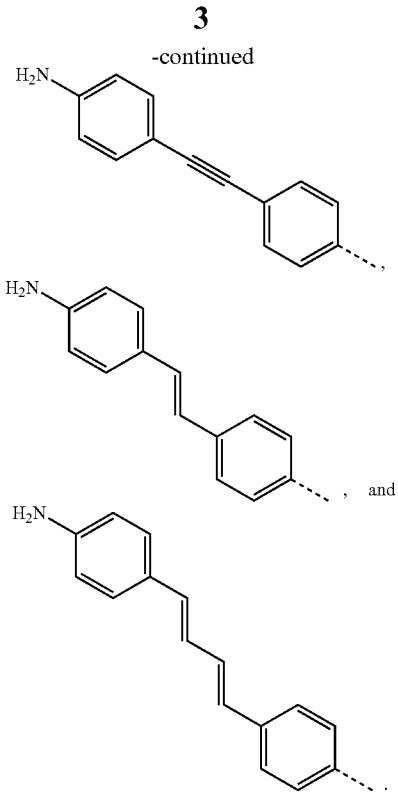

, and

.

In some embodiments, at least 50 wt. % of the fullerene compound are incorporated into the GMA based on the initial weight of the GMA.

In some embodiments, at least 100 wt. % of the fullerene compound are incorporated into the GMA based on the initial weight of the GMA.

Another aspect of the invention relates to a GMA-fullerene composite produced by the method described herein.

In some embodiments, the GMA-fullerene composite is a monolith having a thickness of at least 1 mm.

In some embodiments, the GMA-fullerene composite has an electrical conductivity of at least 10 S/m.

In some embodiments, the GMA-fullerene composite has a mesopore volume of at least 0.5 cm$^3$/g.

In some embodiments, the GMA-fullerene composite has a BET surface area of at least 200 m$^2$/g.

In some embodiments, the GMA-fullerene composite has a Young's modulus of at least 20 MPa.

A further aspect of the invention relates to an electrode comprising the GMA-fullerene composite described herein.

An additional aspect of the invention relates to a supercapacitor comprising the electrode described herein.

In some embodiments, the supercapacitor further comprises an organic or ionic liquid electrolyte in contact with the electrode.

These and other features, together with the organization and manner of operation thereof, will become apparent from the following detailed description when taken in conjunction with the accompanying drawings.

BRIEF DESCRIPTION OF THE DRAWINGS

(FIG. 1A) a GMA-C$_{60}$ composite obtained by noncovalently functionalizing the GMA with 4.5 mM C$_{60}$; (FIG. 1B) CV of a GMA-C$_{60}$ with 13% loading of C$_{60}$ in MeCN/TBAP electrolyte (5 mV/s).

(FIG. 2A) a GMA-PA-C$_{60}$ composite obtained by noncovalently functionalizing the GMA with 7 mM PA-C$_{60}$; (FIG. 2B) CV of a GMA-PA-C$_{60}$ composite with 50% loading of PA-C$_{60}$ in MeCN/TBAP electrolyte (5 mV/s).

DETAILED DESCRIPTION

Figure 1A:
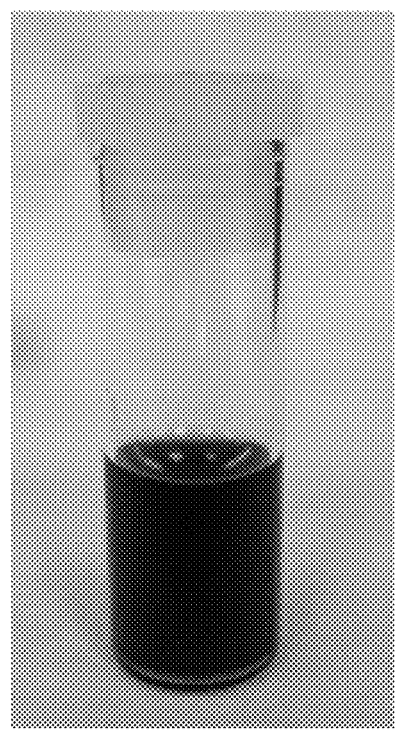
FIGS. 1A-1B.

Reference will now be made in detail to some specific embodiments of the invention contemplated by the inventors for carrying out the invention. Certain examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, well known process operations have not been described in detail in order not to unnecessarily obscure the present invention.

Various techniques and mechanisms of the present invention will sometimes be described in singular form for clarity. However, it should be noted that some embodiments include multiple iterations of a technique or multiple instantiations of a mechanism unless noted otherwise.

INTRODUCTION

The article, "Mechanically Robust 3D Graphene Macroassembly with High Surface Area," Worsley et al., Chem. Commun., 48:8428-8430 (2012), is incorporated by reference in its entirety.

The article, "Toward Macroscale, Isotropic Carbons with Graphene-Sheet-Like Electrical and Mechanical Properties," Worsley et al., Adv. Funct. Mater., 24:4259-4264 (2014), is incorporated by reference in its entirety.

The article, "Synthesis and Characterization of Highly Crystalline Graphene Aerogels," Worsley et al., ACS Nano, 8:11013-11022 (2014), is incorporated by reference in its entirety.

US Patent Publication No. 2012/0034442 to Worsley et al., "Graphene Aerogels," is incorporated by reference in its entirety.

US Patent Publication No. 2014/0178289 to Worsley et al., "High-Density 3D Graphene-Based Monolith and Related Materials, Methods, and Devices," is incorporated by reference in its entirety.

U.S. patent application Ser. No. 14/820,411 to Worsley et al., "Highly Crystalline Graphene Aerogels," is incorporated by reference in its entirety.

Method for Making GMA-Fullerene Composite

Many embodiments of the invention described herein relates to a method for producing a GMA-fullerene composite, comprising providing a GMA comprising a three-dimensional network of graphene sheets crosslinked by covalent carbon bonds, and incorporating at least 20 wt. % of at least one fullerene compound into the GMA based on the initial weight of the GMA to obtain the GMA-fullerene composite.

In some embodiments, the method comprises immersing GMA in a solution of the fullerene compound. In some embodiments, the solution comprises at least one organic solvent. Suitable solvents include, for example, $CS_2$, $CH_2Cl_2$, $CS_2:CH_2Cl_2$, and TNF.

In some embodiments, the concentration of the fullerene compound in the solution is about 1-20 mM, or about 2-15 mM, or about 3-10 mM, or about 4-8 mM.

In some embodiments, the method comprises heating the GMA immersed in a solution of the fullerene compound. In some embodiments, the method comprises heating the GMA immersed in a solution of the fullerene compound at a temperature of 50-100° C. In some embodiments, the method comprises heating the GMA immersed in a solution of the fullerene compound for 12 to 96 hours.

In some embodiments, the method comprises in-situ synthesis of diazonium functionlized fullerene and covalent bonding thereof to GMA.

In some embodiments, the fullerene compound is covalently bound to the graphene sheets. In some embodiments, the methods comprises reacting the GMA with least one fullerene compound represented by $F^*$—$(R^1)_n$, wherein: $F^*$ comprises a fullerene having a surface comprising six-membered and five-membered rings, $R^1$ comprises a reactive group (e.g., diazonium) and a conjugated linker covalently connecting the reactive group to the fullerene, and n is at least one.

In some embodiments, the methods comprises reacting the GMA with least one diazonium functionlized fullerene. In some embodiments, the diazonium functionlized fullerene is represented by

wherein: $F^*$ comprises a fullerene having a surface comprising six-membered and five-membered rings, $R^1$ comprises a diazonium group and a conjugated linker covalently connecting the diazonium group to the fullerene, and n is at least one.

In one embodiment, $F^*$ comprises $C_{60}$. In another embodiment, $F^*$ comprises $C_{70}$. In a further embodiment, $F^*$ comprises $C_{84}$.

In one embodiment, n is 1. In another embodiment, n is 2. In a further embodiment, n is 3 or more.

In one embodiment, $R^1$ is linked to the fullerene by one covalent bond. In another embodiment, $R^1$ is linked to the fullerene by two covalent bonds.

In one embodiment, $R^1$ comprises one reactive group (e.g., diazonium). In another embodiment, $R^1$ comprises two or more reactive groups.

In one embodiment, the diazonium group is represented by

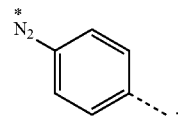

When the counterion is $Cl^-$, the diazonium group can be represented by

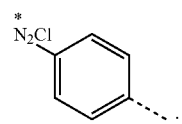

In one embodiment, the conjugated linker of $R^1$ comprises alternating single and multiple bonds. In another embodiment, the conjugated linker of $R^1$ comprises a conjugated hydrocarbon chain. In a further embodiment, the conjugated linker of $R^1$ comprises a conjugated hydrocarbon chain substituted with one or more heteroatoms (e.g., O, S and N).

In one embodiment, the conjugated linker of $R^1$ comprises at least one double bond or alkenylene bridge. In another embodiment, the conjugated linker of $R^1$ comprises at least one triple bond or alkynylene bridge. In a further embodiment, the conjugated linker of $R^1$ comprises at least one aromatic or heteroaromatic ring.

In some embodiments, $R^1$ is selected from the group consisting of

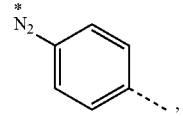

,

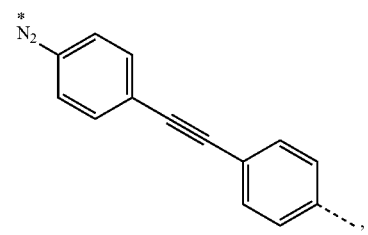

,

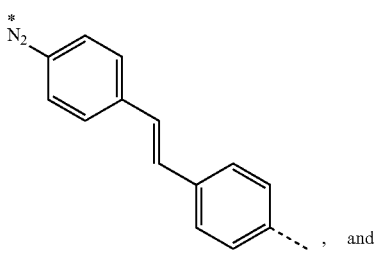

, and

-continued

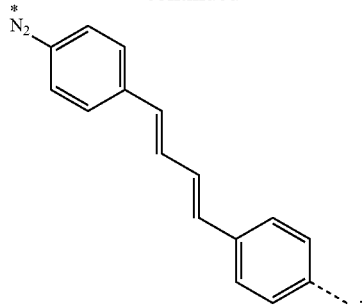

In some embodiments, based on the initial weight of the GMA, at least 40 wt. %, or at least 60 wt. %, or at least 80 wt. %, or at least 100 wt. %, or at least 120 wt. % of the fullerene compound are incorporated into the GMA by covalently bonds.

Alternatively, in some embodiments, the fullerene compound is noncovalently attached to the graphene sheets. In some embodiments, the method comprises incubating the GMA in a solution comprising at least one fullerene compound represented by $F^*—(R^2)_n$, wherein: $F^*$ comprises a fullerene having a surface comprising six-membered and five-membered rings, $R^2$ comprises an aromatic or heteroaromatic group (e.g., phenylamine) and a conjugated linker covalently connecting the aromatic or heteroaromatic group to the fullerene, and n is at least one. In some embodiment, the aromatic or heteroaromatic group comprises 2, 3, 4 or more fused aromatic or heteroaromatic rings.

In some embodiments, the method comprises incubating the GMA in a solution comprising at least one phenylamine functionlized fullerene. In some embodiments, the phenylamine functionlized fullerene is represented by $$F^*—(R^2)_n,$$

wherein: $F^*$ comprises a fullerene having a surface comprising six-membered and five-membered rings, $R^2$ comprises a phenylamine group and a conjugated linker covalently connecting the phenylamine group to the fullerene, and n is at least one.

In one embodiment, n is 1. In another embodiment, n is 2. In a further embodiment, n is 3 or more.

In one embodiment, $R^2$ is linked to the fullerene by one covalent bond. In another embodiment, $R^2$ is linked to the fullerene by two covalent bonds.

In one embodiment, $R^2$ comprises one aromatic or heteroaromatic group (e.g., phenylamine). In another embodiment, $R^2$ comprises two or more aromatic or heteroaromatic groups.

In one embodiment, the phenylamine group is represented by

In one embodiment, the conjugated linker of $R^2$ comprises alternating single and multiple bonds. In another embodiment, the conjugated linker of $R^2$ comprises a conjugated hydrocarbon chain. In a further embodiment, the conjugated linker of $R^2$ comprises a conjugated hydrocarbon chain substituted with one or more heteroatoms (e.g., O, S and N).

In one embodiment, the conjugated linker of $R^2$ comprises at least one double bond or alkenylene bridge. In another embodiment, the conjugated linker of $R^2$ comprises at least one triple bond or alkynylene bridge. In a further embodiment, the conjugated linker of $R^2$ comprises at least one aromatic or heteroaromatic ring.

In some embodiments, $R^2$ is selected from the group consisting of

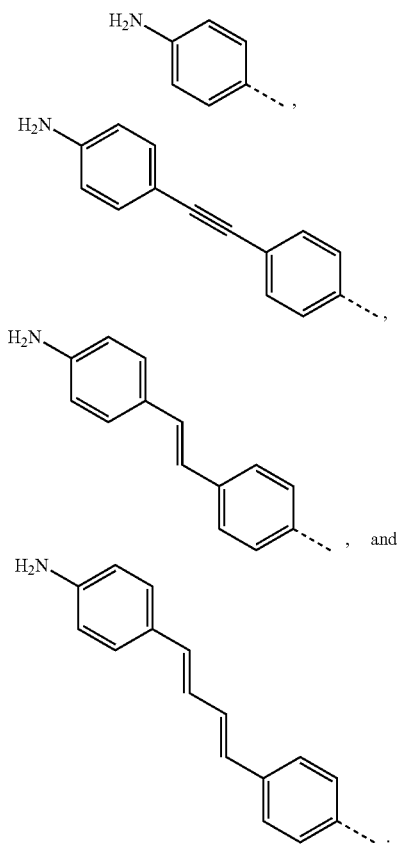

In some embodiments, based on the initial weight of the GMA, at least 20 wt. %, or at least 40 wt. %, or at least 60 wt. %, or at least 80 wt. %, of the fullerene compound are incorporated into the GMA by noncovalently attachment (e.g., physisorption).

In some embodiment, the GMA is a graphene aerogel described in US Patent Publication No. 2012/0034442, which is incorporated by reference in its entirety. In some embodiment, the GMA is a high-density graphene monolith described in US Patent Publication No. 2014/0178289, which is incorporated by reference in its entirety. In some embodiment, the GMA is a highly crystalline grapehen aerogel described in U.S. patent application Ser. No. 14/820,411, which is incorporated by reference in its entirety.

The GMA can comprise, for example, a three-dimensional structure of graphene sheets interconnected or crosslinked by chemical bonds such as covalent carbon-carbon bonds. In some embodiments, 50% or more, or 70% or more, or 80% or more, or 90% or more of the covalent bonds interconnecting the graphene sheets are $sp^2$ carbon-carbon bonds. In some embodiments, 10% or less, or 5% or less, or 3% or less, or 1% or less of the graphene sheets are interconnected only by physical crosslinks. In some embodiments, 10% or less, or 5% or less, or 3% or less, or 1% or less of the graphene sheets are interconnected only by metal crosslinks.

The GMA can be, for example, substantial free of graphene sheets with hydroxyl or epoxide functionalities. In some embodiments, 3% or less, or 1% or less, or 0.5% or less, or 0.1% or less of the carbon atoms in the GMA are connected to a hydroxyl or epoxide functionality. In some embodiments, the atomic oxygen content in the GMA is 10% or less, or 5% or less, or 3% or less, or 1% or less.

In some embodiments, the GMA consists essentially of covalently interconnected graphene sheets. In some embodiments, the GMA is not a macroporous foam. In some embodiments, the GMA is substantially free of a polymer coated on the internal surfaces of the GMA. In some embodiments, the GMA is substantially free of a metal or a metal compound coated on the internal surfaces of the GMA. In some embodiments, the GMA is substantially free of carbon nanoparticles.

GMA-Fullerene Composite

Many embodiments of the invention relate to a GMA-fullerene composite produced by the method described herein.

The weight of the fullerene component compared to the weight of the GMA component can be, for example, at least 20 wt. %, or at least 40 wt. %, or at least 60 wt. %, or at least 80 wt. %, or at least 100 wt. %, or at least 120 wt. %.

The GMA-fullerene composite can be a monolith having a thickness of, for example, at least 100 μm, or at least 1 mm, or at least 10 mm, or at least 100 mm, or about 10 μm to about 1 mm, or about 1 mm to about 100 mm.

The GMA-fullerene composite can have an electrical conductivity of, for example, at least 10 S/m, or at least 20 S/m, or at least 50 S/m, or at least 100 S/m, or at least 200 S/m, or at least 500 S/m, or about 10-1,000 S/m, or about 20-500 S/m, or about 50-200 S/m.

In some embodiments, the GMA-fullerene composite can have a BET surface area of, for example, at least 100 $m^2/g$, or at least 200 $m^2/g$, or at least 300 $m^2/g$, or at least 500 $m^2/g$, or at least 700 $m^2/g$, or about 100-1,500 $m^2/g$, or about 200-1,000 $m^2/g$.

In some embodiments, the GMA-fullerene composite can have a Young's modulus of, for example, at least 10 MPa, or at least 20 MPa, or least 50 Mpa, or at least 100 MPa, or at least 200 MPa, or at least 500 MPa, or about 10-1,000 MPa, or about 20-500 MPa.

In some embodiments, the GMA-fullerene composite can have a mesopore volume of, for example, at least 0.2 $cm^3/g$, or at least 0.5 $cm^3/g$, or at least 0.8 $cm^3/g$, or at least 1 $cm^3/g$, or at least 1.2 $cm^3/g$, or at least 1.5 $cm^3/g$, or about 0.2-5 $cm^3/g$, or about 0.5-3 $cm^3/g$.

In some embodiments, the GMA-fullerene composite comprises at least one fullerene compound covalently connected to at least one graphene sheet via at least one conjugated linker. In one embodiment, the conjugated linker comprises alternating single and multiple bonds. In another embodiment, the conjugated linker comprises a conjugated $C_1$-$C_{30}$, $C_1$-$C_{20}$, $C_1$-$C_{15}$, or $C_1$-$C_{10}$ hydrocarbon chain. In a further embodiment, the conjugated linker comprises a conjugated $C_1$-$C_{30}$, $C_1$-$C_{20}$, $C_1$-$C_{15}$, or $C_1$-$C_{10}$ hydrocarbon chain substituted with one or more heteroatoms (e.g., O, S and N). In one embodiment, the hydrocarbon chain comprises at least one double bond or alkenylene bridge. In another embodiment, the hydrocarbon chain comprises at least one triple bond or alkynylene bridge. In a further embodiment, the hydrocarbon chain comprises at least one aromatic or heteroaromatic ring.

Electrode and Supercapacitor

The GMA-fullerene composite described herein can be used in a variety of applications, including supercapacitors, battery electrodes, electrical energy storage, micro-batteries, hybrid capacitors, next-generation batteries, hybrid vehicles, and alternative energy storage.

The GMA-fullerene composite described herein is functionally advantageous in energy storage applications. In particular, $C_{60}$ can store up to 6 electrons, or 1 $e^-$/10 carbon atoms (Echegoyen et al., *Acc. Chem. Res.*, 1998, 31, 593-601), compared with 1 $e^-$/100 carbon atoms for graphitic carbon materials (Berger et al., *J. Phys. Chem. B*, 2004, 108(52):19912-19916; Sarma et al., *Rev. Mod. Phys.*, 2011, 83(2):407-470; Wood et al., *J. Phys. Chem. C*, 2014, 118(1):4-15), a 10-fold increase in electrical storage capacity. In principle a graphene aerogel functionalized with 50 wt % loading of fullerene could achieve 4× greater energy storage compared with an unfunctionalized graphene aerogel. The measured capacity of an unfunctionalized graphene aerogel electrode is ~60 coulombs per gram (C/g) (Campbell et al., *J. Mater. Chem. A*, 2014, 2:17764-17770). With fullerene functionalization (e.g., ~50 wt % loading), an electron storage capacity of at least about 100 C/g, or at least about 150 C/g, or at least about 200 C/g, or at least about 250 C/g, or at least about 300 C/g, or at least about 350 C/g, or at least about 400 C/g, or about 100-500 C/g, or about 200-400 C/g, can be achieved. With higher fullerene loading (e.g., through the use of different length linkers), an electron storage capacity of up to about 600 C/g, or up to about 550 C/g, or up to about 500 C/g, or about 200-600 C/g, or about 300-500 C/g, or about 400-600 C/g, can be achieved. The theoretical maximum electron storage capacity for $C_{60}$ is 803 C/g—the equivalent of 222.5 mAh/g, which is approaching the capacity of lithium ion battery cathode materials (e.g., $LiCoO_2$ theoretical max is 274 mAh/g).

Accordingly, many embodiments of the invention described herein also relate to an electrode comprising the GMA-fullerene composite, as well as a supercapacitor comprising the electrode.

In one embodiment, the supercapacitor further comprises an organic liquid electrolyte in contact with the electrode. In another embodiment, the supercapacitor further comprises an ionic liquid electrolyte with the electrode. In an additional embodiment, the supercapacitor further comprises an aqueous electrolyte with the electrode.

Unlike anthraquinone and other redox-based charge-storage strategies that involve chemical reactions (proton-coupled electron transfer), fullerenes store charge in a purely electric double-layer capacitance (EDLC) mechanism that is an interfacial phenomenon and does not involve a chemical reaction, which means that charge/discharge rates can be faster and long-term stability will increase. Moreover, because the purely EDLC mechanism does not require protons, the GMA-fullerene composite described herein can be used in supercapacitors in combination with organic or ionic liquid electrolytes, which greatly increases the operational voltage window and thus the total energy stored ($E=\frac{1}{2} CV^2$).

WORKING EXAMPLES

Example 1—Synthesis of GMA

Graphene macro-assemblies (GMA) were prepared in a similar manner to what were previously reported in Worsley et al., *Chem. Commun.*, 48:8428-8430 (2012), which is incorporated herein by reference. Graphene oxide (GO, 1-2 layer, 300-800 nm diameter sheets) was purchased from Cheaptubes and used as received. GO was dispersed in Milli-Q $H_2O$ (20 mg/mL) by ultrasonication for 24 h, and ammonium hydroxide catalyst (211 μL/g) was added to the resulting suspension. The GO suspension/catalyst mixture was cast into disk shaped molds, sealed, and placed in a 75° C. oven for 72 h for crosslinking/gelation. The monolithic disks were washed in water, followed by acetone, and dried with supercritical $CO_2$. The disks were then carbonized at 1050° C. for 3 h under flowing $N_2$ to remove oxygen functionality (final O content <2 at. %). The resulting GMA disks are approximately 1 cm in diameter by 250 μm thickness, weigh ~1 mg, have density of ~0.07 $g/cm^3$, and have a BET surface area of ~1300 $m^2/g$.

Example 2—Synthesis of 1-(4-aminophenyl)ethano-p-toluenesulfonyl hydrazone

A mixture of 1-(4-aminophenyl)ethano (1.0 g, 3.36 mmol) and p-toluenesulfonyl hydrazone (2.2 g, 11.88 mmol) in MeOH (20 mL) was stirred and refluxed for 2 days. The mixture was left without heating for 1 day and then cooled to −10° C. The white powder was then filtered and washed with cold MeOH and dichloromethane, and dried under vacuum (65% yield).

Example 3—Synthesis of 1-(4-aminophenyl)ethano-$C_{60}$ (PA-$C_{60}$)

Diazo addend was prepared in-situ by dissolving 1-(4-aminophenyl)ethano-p-toluenesulfonyl hydrazone (122.7 mg, 0.208 mmol) in 1.2 mL of anhydrous pyridine under $N_2$ atmosphere. NaOMe (56.3 mg, 1.042 mmol) was added, and the mixture was stirred for 30 min. A solution of 75.0 mg of $C_{60}$ (0.1042 mmol) in 7 mL of o-DCB (aka, 1,2-dichlorobenzene) was added and stirred at 110 C for 6 h. The solvent from the reaction mixture was removed under nitrogen and the crude product was purified by silica gel column using initially $CS_2$ as the eluent to collect the unreacted [60] fullerene, followed by $CS_2:CH_2Cl_2$ 1:1 to collect the monoadduct (41%).

Example 4—Synthesis of 1-(4-diazoniumphenyl)ethano-C60 tetrafluoroborate

Diazonium salt was prepared by dissolving 1-(4-aminophenyl)ethano-$C_{60}$ in a 5:1 mixture of $CH_3CN:CH_2Cl_2$ under $N_2$ atmosphere, the solution was cold down to −30 C and nitrosonium tetrafluoroborate ($NOBF_4$) was added. The mixture was stirred for 1.5 h. The solvent from the reaction mixture was removed under reduced pressure and the crude product was purified by washing the crude mixture with $CS_2:CH_2Cl_2$ 7:3 to remove the unreacted monoadduct.

Example 5—Noncovalent Functionalize of GMA with $C_{60}$

Figure 1B:
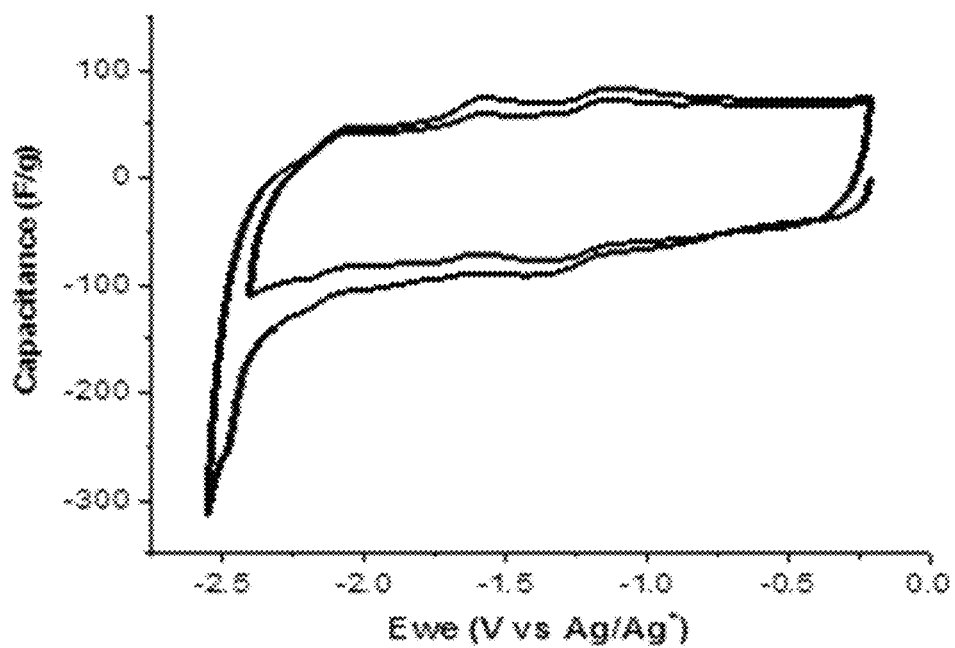

GMA was non-covalently functionalized with $C_{60}$ via physisorption. The following loading percentages based on the initial weight of the GMA were achieved.
  4.5 mM $C_{60}$ in $CS_2$, 3 days=16% loading
  4 mM $C_{60}$ in $CS_2$, 15 h=13% loading
  2 mM $C_{60}$ in $CS_2$, 15 h=5% loading
FIG. 1A shows a GMA-$C_{60}$ composite obtained by non-covalently functionalizing the GMA with 4.5 mM $C_{60}$, and FIG. 1B shows CV of a GMA-$C_{60}$ composite with 13% loading of $C_{60}$ in MeCN/TBAP electrolyte (5 mV/s).

Example 6—Noncovalent Functionalize of GMA with PA-$C_{60}$

Figure 2A:
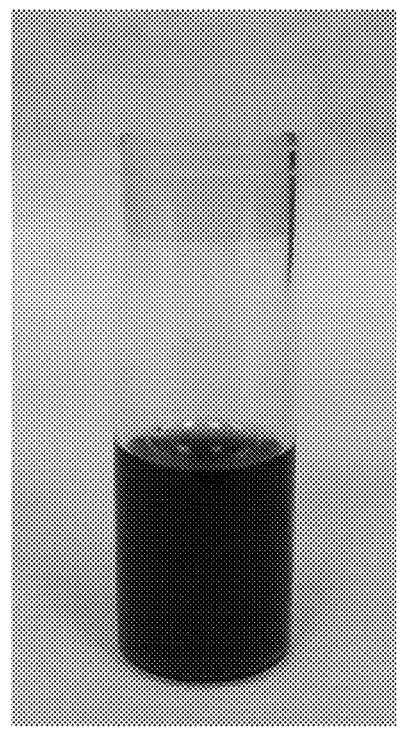
FIGS. 2A-2B.
Figure 2B:
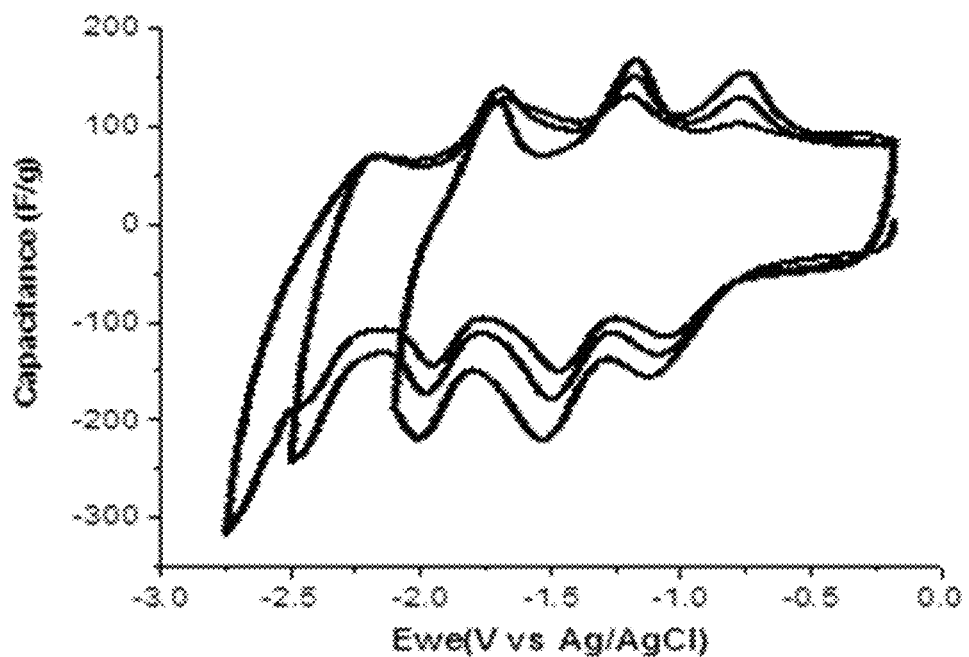

GMA was non-covalently functionalized with PA-$C_{60}$ via physisorption. PA-$C_{60}$ is more soluble than unmodified $C_{60}$. The following loading percentages based on the initial weight of the GMA were achieved.
  7 mM PA-$C_{60}$ in $CS_2:CH_2Cl_2$ 7:3, 3 days=87% loading
  6 mM PA-$C_{60}$ in $CS_2:CH_2Cl_2$ 7:3, 17 h=50% loading
  4 mM PA-$C_{60}$ in $CS_2:CH_2Cl_2$ 7:3, 14 h=26% loading
  2.1 mM PA-$C_{60}$ in $CS_2:CH_2Cl_2$ 7:3, 14 h=16% loading
FIG. 2A shows a GMA-PA-$C_{60}$ composite obtained by noncovalently functionalizing the GMA with 7 mM PA-$C_{60}$, and FIG. 2B shows CV of a GMA-PA-$C_{60}$ composite with 50% loading of PA-$C_{60}$ in MeCN/TBAP electrolyte (5 mV/s).

Example 7—Covalent Functionalization of GMA with Diazonium-$C_{60}$

GMA was added to a 1 mM solution of diazonium-$C_{60}$ in THF, and heat at 60° C. for 2 days. A final loading of 67% based on the initial weight of the GMA was achieved.

Example 8—In-Situ Synthesis of Diazonium-$C_{60}$ and Covalent Functionalization of GMA To a 4 mM solution of PA-$C_{60}$ in o-DCB:MeCN 4:1, 2 drops of isopentyl nitrite were added and a precipitate was observed immediately. GMA was then added and heated at 85° C. over the weekend. After the weekend the precipitate and solution were removed and GMA was washed several times with $CS_2$, $CH_2Cl_2$ and THF to remove not chemically bonded fullerene. GMA was then left in THF overnight and dried in the oven at 80° C. for 2 days. A final loading of 138% based on the initial weight of the GMA was achieved.

Figure 3:
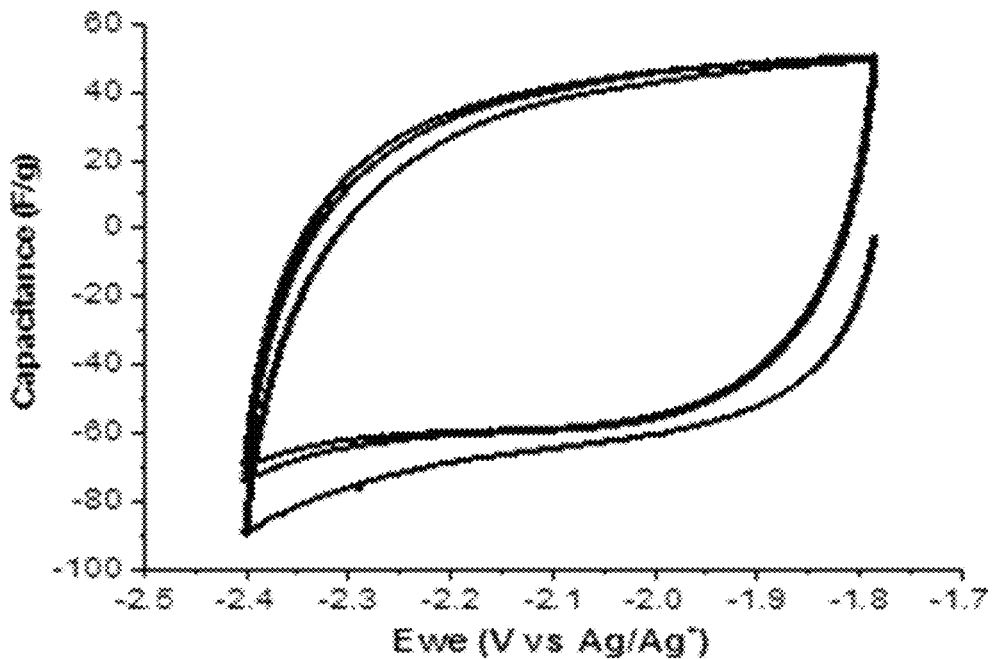
FIG. 3: CV of a non-functionalized GMA in MeCN/TBAP electrolyte (5 mV/s).
Figure 4:
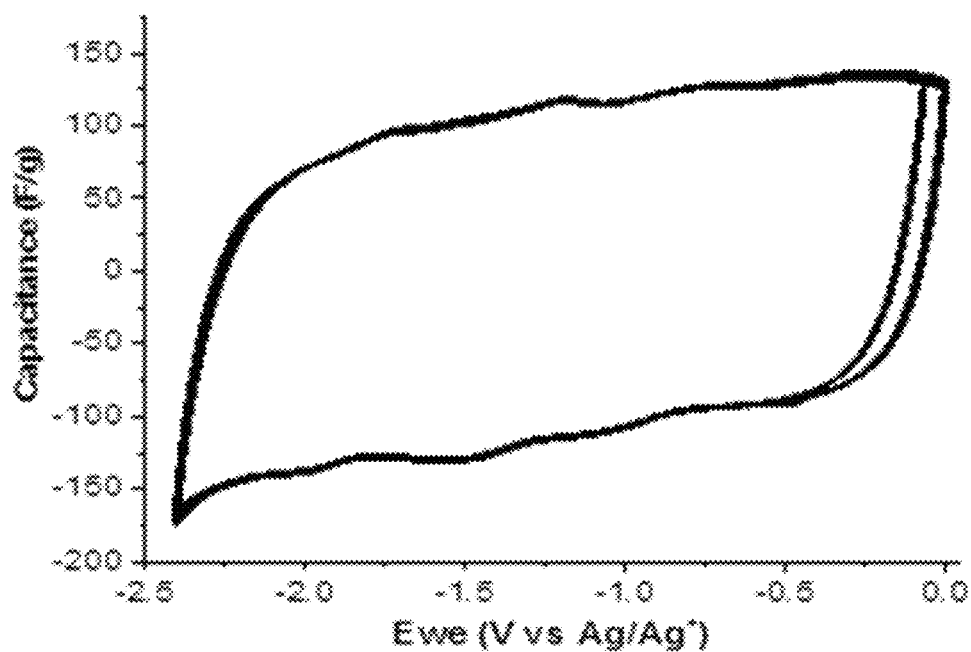
FIG. 4: CV of a GMA-fullerene composite with a final loading of 138% in MeCN/TBAP electrolyte (10 mV/s). This GMA-fullerene composite was obtained by covalently functionalizing the GMA with diazonium-C$_{60}$.
Figure 5:
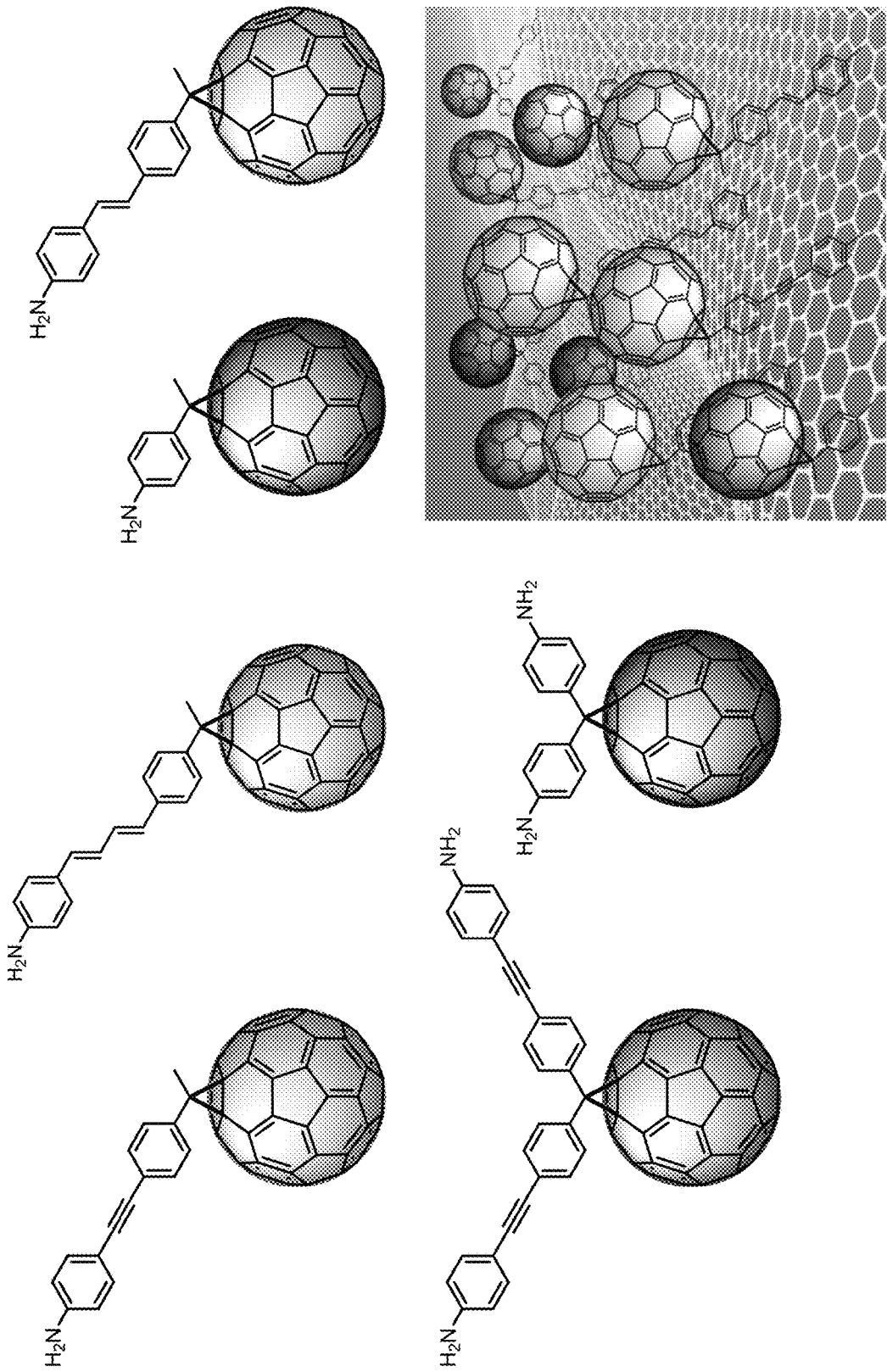
FIG. 5: Examples of phenylamine-functionalized fullerene compounds for functionalization of GMA.
Figure 6:
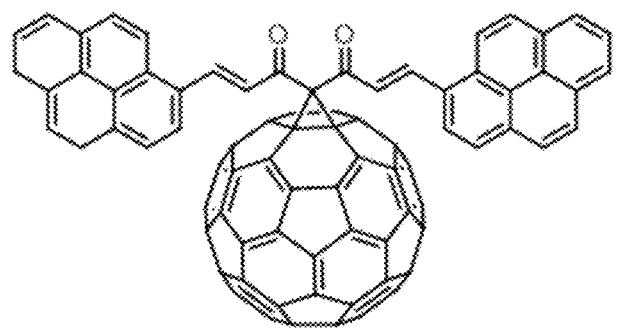
FIG. 6: Additional examples of fullerene compounds for functionalization of GMA.
Figure 6:
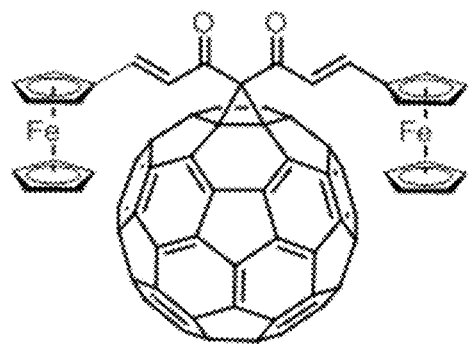
Figure 6:
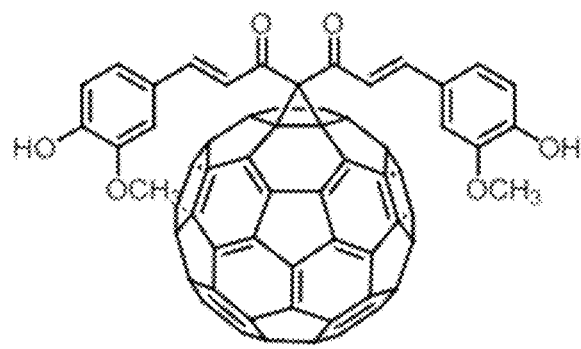
Figure 7:
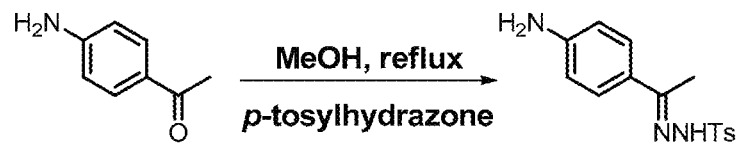
Figure 8:
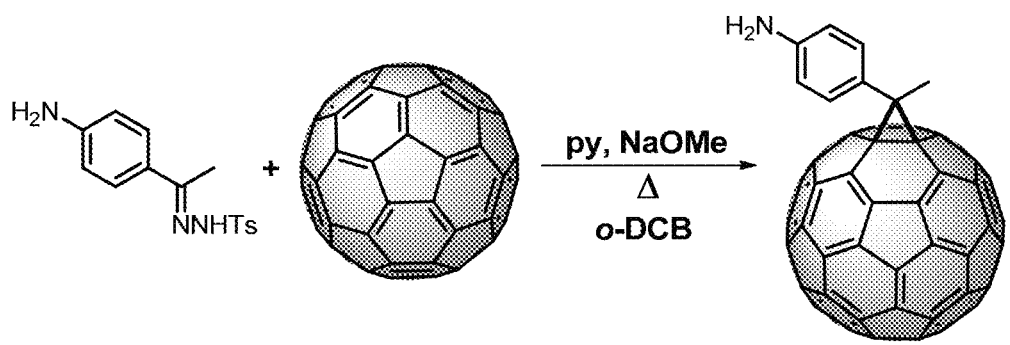
Figure 9:
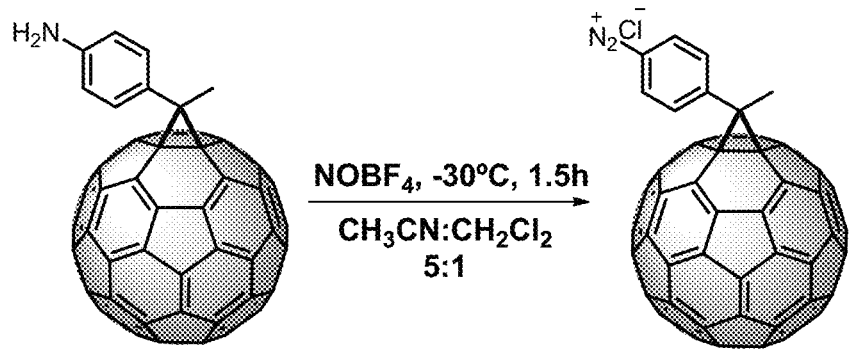
Figure 10:
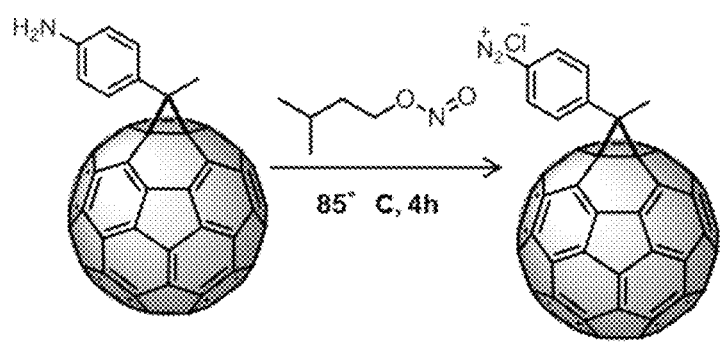

FIG. 4 shows CV of a GMA-fullerene composite with 138% loading of diazonium-$C_{60}$ in MeCN/TBAP electrolyte (10 mV/s), which is evidently functionally superior compared to CV of a non-functionalized GMA in MeCN/TBAP electrolyte (5 mV/s) as shown in FIG. 3.

As used herein, the singular terms "a," "an," and "the" include plural referents unless the context clearly dictates otherwise. Thus, for example, reference to a compound can include multiple compounds unless the context clearly dictates otherwise.

As used herein, the terms "substantially," "substantial," and "about" are used to describe and account for small variations. When used in conjunction with an event or circumstance, the terms can refer to instances in which the event or circumstance occurs precisely as well as instances in which the event or circumstance occurs to a close approximation. For example, the terms can refer to less than or equal to ±10%, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations, which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scopes of this invention.

What is claimed is:

1. A method for producing a graphene macro-assembly (GMA)-fullerene composite, comprising providing a GMA comprising a three-dimensional network of graphene sheets crosslinked by covalent carbon bonds, and incorporating at least 20 wt. % of at least one fullerene compound into the GMA based on the initial weight of the GMA to obtain the GMA-fullerene composite, wherein the fullerene compound is covalently bound to the graphene sheets.

2. The method of claim 1, wherein the incorporating step comprises reacting the GMA with least one diazonium functionlized fullerene.

3. The method of claim 2, wherein the diazonium functionlized fullerene is represented by: $F^*-(R^1)_n$, wherein:
F* comprises a fullerene having a surface comprising six-membered and five-membered rings,
$R^1$ comprises a diazonium group and a conjugated linker covalently connecting the diazonium group to the fullerene, and
n is at least one.

4. The method of claim 3, wherein n is 1 or 2, F* is $C_{60}$ or $C_{70}$, and $R^1$ is selected from the group consisting of

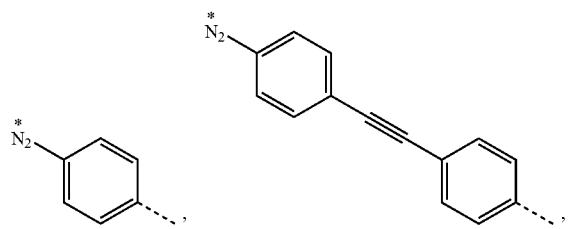

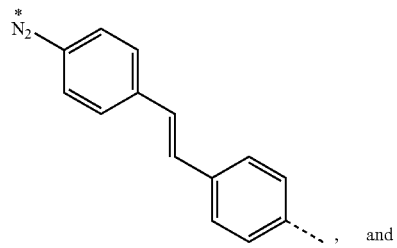

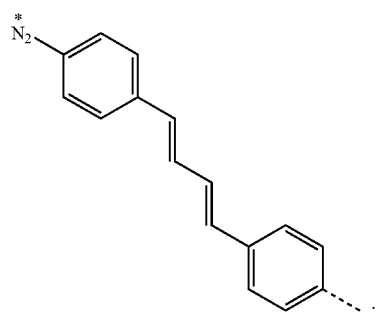

5. The method of claim 1, wherein based on the initial weight of the GMA at least 50 wt. % of the fullerene compound are incorporated into the GMA.

6. The method of claim 1, wherein based on the initial weight of the GMA at least 100 wt. % of the fullerene compound are incorporated into the GMA.

7. A method for producing a graphene macro-assembly (GMA)-fullerene composite, comprising providing a GMA comprising a three-dimensional network of graphene sheets crosslinked by covalent carbon bonds, and incorporating at least 20 wt. % of at least one fullerene compound into the GMA based on the initial weight of the GMA to obtain the GMA-fullerene composite, wherein the fullerene compound is noncovalently attached to the graphene sheets, and wherein the incorporating step comprises incubating the GMA in a solution comprising at least one phenylamine functionlized fullerene.

8. The method of claim 7, wherein the phenylamine functionlized fullerene is represented by: $F^*-(R^2)_n$, wherein:
F* comprises a fullerene having a surface comprising six-membered and five-membered rings,
$R^2$ comprises a phenylamine group and a conjugated linker covalently connecting the phenylamine group to the fullerene, and
n is at least one.

9. The method of claim 8, wherein n is 1 or 2, F* is $C_{60}$ or $C_{70}$, and $R^2$ is selected from the group consisting of

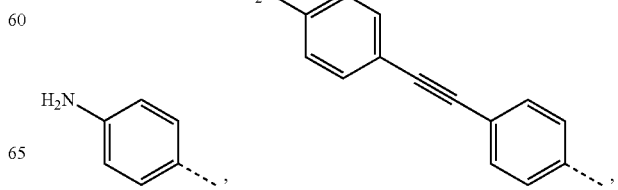

-continued

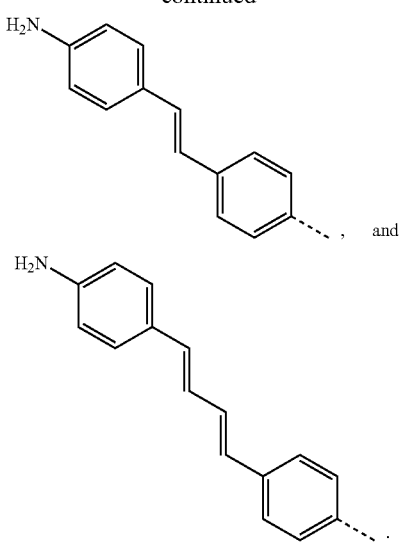

10. A GMA-fullerene composite produced by the method of claim 1.

11. The GMA-fullerene composite of claim 10, wherein the GMA-fullerene composite is a monolith having a thickness of at least 1 mm.

12. The GMA-fullerene composite of claim 10, wherein the GMA-fullerene composite has an electrical conductivity of at least 10 S/m.

13. The GMA-fullerene composite of claim 10, wherein the GMA-fullerene composite has a mesopore volume of at least 0.5 $cm^3/g$.

14. The GMA-fullerene composite of claim 10, wherein the GMA-fullerene composite has a BET surface area of at least 200 $m^2/g$.

15. The GMA-fullerene composite of claim 10, wherein the GMA-fullerene composite has a Young's modulus of at least 20 MPa.

16. A supercapacitor comprising an electrode comprising the GMA-fullerene composite of claim 10, and further comprising an organic or ionic liquid electrolyte in contact with the electrode.

17. A GMA-fullerene composite produced by the method of claim 7.

18. A supercapacitor comprising an electrode comprising the GMA-fullerene composite of claim 17, and further comprising an organic or ionic liquid electrolyte in contact with the electrode.

* * * * *